(12) United States Patent
Hwang

(10) Patent No.: US 6,696,404 B1
(45) Date of Patent: Feb. 24, 2004

(54) ANTIBACTERIAL COMPOSITION HAVING XANTHORRIZOL

(75) Inventor: Jae-Kwan Hwang, Koyang-shi (KR)

(73) Assignee: LG Household & Healthcare (KR)

( * ) Notice: Subject to any disclaimer, the term of this patent is extended or adjusted under 35 U.S.C. 154(b) by 0 days.

(21) Appl. No.: 10/312,134

(22) PCT Filed: May 8, 2000

(86) PCT No.: PCT/KR00/00432

§ 371 (c)(1),
(2), (4) Date: Dec. 19, 2002

(87) PCT Pub. No.: WO00/67711

PCT Pub. Date: Nov. 16, 2000

(30) Foreign Application Priority Data

| | | |
|---|---|---|
| May 8, 1999 | (KR) | 1999/0016507 |
| Oct. 6, 1999 | (KR) | 1999/0043143 |
| Oct. 13, 1999 | (KR) | 1999/0044406 |
| Nov. 13, 1999 | (KR) | 1999/0050486 |

(51) Int. Cl.[7] ............... C11D 3/38; C11D 3/48; C11D 7/50; A61K 7/16; A61K 7/50
(52) U.S. Cl. ......... 510/386; 510/130; 510/382; 510/463; 510/565; 514/731; 514/733
(58) Field of Search ............... 510/130, 382, 510/386, 463, 565; 514/731, 733

(56) References Cited

U.S. PATENT DOCUMENTS 5,411,733 A    5/1995   Hozumi et al.

2003/0082244 A1 * 5/2003 Yoshida et al. ............ 424/725

FOREIGN PATENT DOCUMENTS

| EP | 0568001 | 7/1995 |
| JP | 9-157144 | 6/1997 |
| WO | WO 88/05304 | 7/1988 |

OTHER PUBLICATIONS

Kikuzuzaki H., et al; Structure of Antioxidative compounds in Ginger 1994, Food Phytochemicals for Cancer Prevention II, ACS Symposium Series No. 547, pp. 237–243.*

* cited by examiner

Primary Examiner—Mark Kopec
Assistant Examiner—John M. Petruncio
(74) Attorney, Agent, or Firm—Cantor Colburn LLP

(57) ABSTRACT

An antibacterial composition having xanthorrizol is provided. The xanthorrizol is prepared by obtaining crude extract having antibacterial activity from *Curcuma xanthorriza* Roxb. lysate by the aid of solvent extraction, supercritical fluid extraction, microwave extraction or ultrasonic extraction; applying the crude extract to chromatography to obtain active fraction; acetylation of the active fraction to change its polarity and applying to chromatography to isolate an acetylated single compound; and, deacetylation of the acetylated single compound to give xanthorrizol having antibacterial activity. Since xanthorrizol has potential antibacterial activity over a broad spectrum of microorganisms under a wide range of temperature, it can be practically applied to antibacterial agent, tooth paste, oral cleanser, chewing gum, soap and cosmetics which require the antibacterial activity.

17 Claims, 3 Drawing Sheets

ANTIBACTERIAL COMPOSITION HAVING XANTHORRIZOL

BACKGROUND OF THE INVENTION

1. Field of the Invention

The present invention relates to a process for preparing xanthorrizol and novel uses of the same, more specifically, to a process for preparing xanthorrizol from *Curcuma xanthorriza* Roxb. and uses of xanthorrizol as active ingredients for antibacterial agent, tooth paste, oral cleanser, chewing gum, soap and cosmetics.

2. Description of Related Art

Caries and periodontal disease are infectious dental diseases which are primarily caused by dental pathogens such as *Streptococcus mutans, Streptococcus sorbrinus, Actinomyces viscosus* and *Porphyromonas gingivalis*(see: Marsh P. D., et al., J. Dent. Res., 71:1431–1438, 1992). To prevent and treat these caries and periodontal disease, antibiotics such as spiramycin, vancomycin and chlorohexidine, and organic/inorganic fluoride have been conventionally used in the art. The conventional antibiotics are, however, proven to be less satisfactory in a sense that they may cause untoward effects such as drug resistance, diarrhea and emesis. Moreover, sodium chloride, antiplasmin, allantoin derivatives, vitamins and amino acids, which are major active ingredients for oral cleanser, are not sufficient enough for removing pathogens on teeth surface. Particularly, it has been well known that sodium chloride possesses preventive and curable effects on caries and periodontal disease. However, it has also revealed a shortcoming that it notably reduces foaming power of anionic surfactant whose main purpose is to facilitate cleansing effect, and lacks full satisfaction in terms of refresh feeling due to its salty taste. Natually, many researchers have tried to deveop the alternative substances with no adverse effects, for eradication of pathogens causing caries and peridontal disease.

On the other hand, acne, athlete's foot, itchiness and eczema are caused by skin infectious pathogens such as *Propionibacterium acnes, Candida albicans, Staphylococcus aureus* and *Staphylococcus epidermis*(see: Raman A., et al., Lett. Appl. Microbiol., 21:242–245, 1995). To inhibit the said skin infectious pathogens, benzoyl peroxide, salicylic acid, benzalkonium chloride and antibiotics such as erythromycin, and natural products such as tea tree oil, royal jelly extract and ginseng extract have been used in the art. While the antibiotics may have some positive effects on the treatment of skin infections, they may cause drug resistance and other adverse effects such as rash and inflammation, which naturally limits their practical use(see: Gollnick H., et al., J. Dermatology, 196:119–125, 1998). Moreover, upon therapeutic application for dermal diseases or cosmetics, antibiotics derived from natural resources may cause unexpected decline in their efficacy, since they are not single compounds. Also, application of these natural products has a certain limitation since they have a narrow spectrum of antibacterial activity, and their activities may be decreased by evaporation or degradation at high temperature caused by weak thermal stability(see: Higaki S., et al.,J. Dermatology, 23:310–314, 1996). Under the circumstances, there are strong reasons for exploring and developing substances having high antibacterial activity on skin infections with no adverse effects from natural products such as medicinal plants.

SUMMARY OF THE INVENTION

The present inventors have made efforts to develop a substance from natural source which can efficiently inhibit the dental infections and skin diseases, and finally discovered that: xanthorrizol prepared from *Curcuma xanthorriza* Roxb. has a wide spectrum of antibacterial activity, heat stability and safety onto human skin; and, therefore, it can be applied in antibacterial agent, tooth paste, oral cleanser, soap and cosmetics which require antibacterial activity.

The present invention provides a process for preparing xanthorrizol from *Curcuma xanthorriza* Roxb. and an antibacterial composition having xanthorrizol.

The invention provides a process for using xanthorrizol as an active ingredient of antibacterial agent.

The invention provides a process for using xanthorrizol as an active ingredient of tooth paste.

The invention provides a process for using xanthorrizol as an active ingredient of oral cleanser.

The invention provides a process for using xanthorrizol as an active ingredient of chewing gum.

The invention provides a process for using xanthorrizol as an active ingredient of antibacterial soap.

The invention provides a process for using xanthorrizol as an active ingredient of cosmetics.

BRIEF DESCRIPTION OF THE DRAWINGS

The above and the other objects, and features of the present invention will become apparent from the following descriptions given in conjunction with the accompanying drawings, in which.

DETAILED DESCRIPTION OF THE INVENTION

Figure 1:
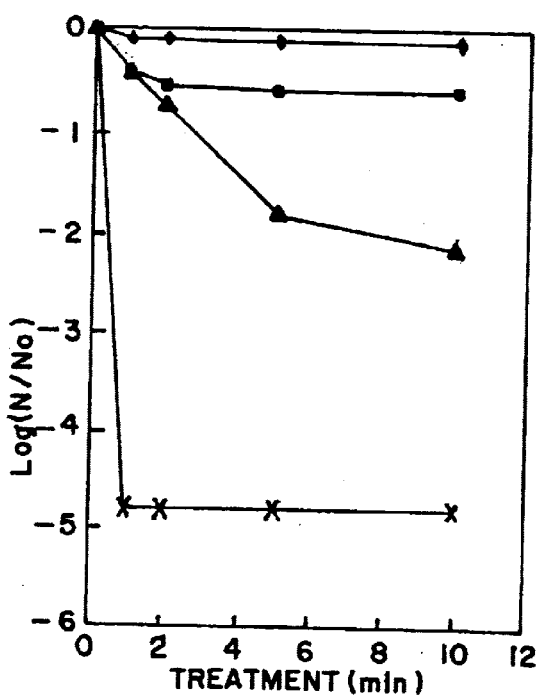
FIG. 1 is a graph showing antibacterial activity of crude extract from *Curcuma xanthorriza* Roxb. against *Streptococcus mutans* in terms of viable cell count.

The process for preparing xanthorrizol of the present invention comprises the steps of: obtaining crude extract having antibacterial activity from *Curcuma xanthorrhiza* Roxb. by the aid of solvent extraction, supercritical fluid extraction, microwave extraction, or ultrasonication; applying the crude extract thus isolated to a column chromatography to obtain active fraction; acetylating the active fraction and applying the said fraction to a column chromatography to isolate an acetylated single compound; and, deacetylating the acetylated single compound to give xanthorrizol having antibacterial activity.

The process for preparing xanthorrizol of present invention comprises the following steps:

Step 1: Isolation of Crude Extract

Lysate of *Curcuma xanthorriza* Roxb. is extracted by one of extraction methods employing organic solvent, supercritical fluid, microwave or ultrasonic wave, and subsequently extracted again with ethylacetate to isolate crude extract having antimicrobial activity. The solvent extraction is carried out by employing an organic solvent of methanol, ethanol, hexane, ethylacetate or chloroform; water; or, mixtures thereof, preferably, water or 50 to 100%(v/v) methanol, ethanol or hexane, most preferably, 50 to 100%(v/v) methanol. The supercritical fluid extraction is performed by employing a supercritical fluid of carbon dioxide at 35 to 70° C. under a pressure of 100 to 400 bar; the microwave extraction, by employing a solvent of water, methanol, ethanol or hexane under a microwave condition of 2,450 MHz for 1 to 10 minutes at 50 to 120° C.; and, the ultrasonic extraction, by employing a solvent of water, methanol, ethanol or hexane under an ultrasonic condition of 48 kHz for 10 to 60 minutes at 15 to 50° C. The crude extract is filtrated using Whatman filtering paper, condensed using rotary evaporator under a reduced pressure to remove the solvent, further extracted with ethylacetate, and condensed again using rotary evaporator under a reduced pressure to give crude extract having antibacterial activity.

Step 2: Silica Gel Chromatography(I)

The crude extract prepared in the previous step is applied to a column chromatography to obtain active fraction with antibacterial activity: silica gel is employed as a resin for the chromatography and elution is made by a solvent mixture of hexane and ethylacetate, hexane and chloroform, or hexane and benzene, preferably, a mixture of hexane and ethylacetate(1:1 to 50:1(v/v)), most preferably, a mixture of hexane and ethylacetate(1:1 to 10:1(v/v)), and optionally stepwise elution by changing a mixing ratio of solvents with the lapse of time.

Step 3: Acetylation/Chromatography(II)

The active fraction obtained in the previous step is acetylated and applied to a column chromatography again to isolate a single compound having antibacterial activity. The acetylation is carried out by dissolving the fraction in pyridine, adding the equal volume of acetic anhydride, and reacting for more than 15 hours, preferably, 15 to 36 hours at room temperature. Then, the silica gel chromatography is carried out to isolate an acetylated single compound with antibacterial activity by employing a mixture of hexane and ethylacetate, hexane and chloroform, hexane and benzene, or mixtures of other organic solvents, preferably, a mixture of hexane and ethylacetate(5:1 to 50:1(v/v)).

Step 4: Deacetylation for Obtaining Xanthorrizol

The acetylated single compound isolated in the previous step is dissolved in methanol, deacetylated by the addition of KOH, and neutralized by applying it onto a cation-exchange resin to give xanthorrizol having antibacterial activity. Preferably, concentration of KOH is controlled at a range of 3 to 7%, and the deacetylation is performed for more than 2 hours, preferably 2 to 4 hours, most preferably 3 hours.

By analyzing functional groups with $^1$H-NMR, $^{13}$C-NMR (4000 MHz, $CDCl_3$) IR, and measuring molecular weight with EIMS(electronic isolation mass spectrometry), the purified single compound was finally identified as xanthorrizol, a kind of sequiterpenoids having biasabolane structure represented by the following formula.

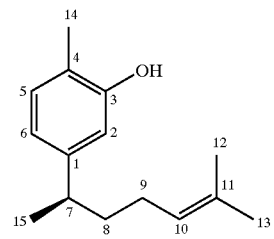

Based on the measurement of MIC value, xanthorrizol of the present invention was proven to show strong antibacterial activity over a broad spectrum of microorganisms. Well diffusion assay also revealed that it is highly stable at a high temperature. In addition, xanthorrizol was found to have safety through patch test onto human skin. Therefore, xanthorrizol of the present invention, with its strong antibacterial activity and safety, may be formulated into antibacterial agent, tooth paste, oral cleanser, chewing gum, soap and cosmetics which require antibacterial activity.

To prepare the antibacterial agent of the present invention, xanthorrizol may be formulated into tablet, capsule, soft gelatin capsule, solution, ointment, plaster, granule, lotion, aerosol, suppository, cataplasma, cream, troche, paste, pill and injection by mixing it with pharmaceutically acceptable carriers such as polyvinylpyrrolidone and hydroxypropylcellulose; disintegrators such as calcium carboxymethylcellulose and sodium glycolate starch; diluents such as corn starch, lactose, soy bean oil, cellulose crystal and mannitol; lubricants such as magnesium stearic acid and talc; sweeteners such as sugar, fructose, sorbitol and aspartame; stabilizers such as sodium carboxymethylcellulose, $\alpha$ or $\beta$ cyclodextrin, vitamin C, citric acid, white wax; preservatives such as methyl p-oxybenzoic acid, propyl p-oxybenzoic acid and sodium benzoic acid; and spice such as ethyl vaseline, masking flavor, menthol and herb. These antibacterial agents may serve as effective therapy for dental caries, periodontal disease, acne, athlete's foot, itchiness and eczema.

Xanthorrizol having antibacterial activity may be applied in the preparation of tooth paste, oral cleanser and chewing gum. For example, in case of oral cleanser, it may comprise xanthorrizol as an active ingredient in a concetration of 0.0001 to 0.1%(w/w) together with the conventional ingredients for oral cleansers such as abrasive, binder, foamer, spice, sweetner, buffer and alcohol. Similarly, tooth paste can be formulated comprising xanthorrizol in a concentration of 0.001 to 1.0%(w/w) with the ingredients such as abrasive, fluoride compound as an additional active ingredient, binder, foamer, spice, sweetener and buffer. For the preparation of chewing gum, it may further comprise ingredients such as gum base, sugar powder, glucose, starch hydrolysate, glycerin and spice.

Moreover, antibacterial soap containing xanthorrizol may be manufactured by employing conventional soap base which include fat, coconut oil, palm oil and glycerin, together with spice, pigments, antioxidants, and moisteners. The content of xanthorrizol in the antibacterial soap is preferred in a range of 0.001 to 5.0%(w/w) for the following reasons: less than 0.001% of xanthorrizol may decrease antibacterial and disinfectant activity which in turn reduces its efficiency on eczema, itchiness, acne and freckle, while more than 5.0% may reduce the synergic effects on the whole and decrease the cleansing effects due to relative low contents of soap base.

Meanwhile, cosmetics such as facial lotion and cream can be manufactured by containing xanthorrizol in a concentration of 0.001 to 1.0%(w/w), wherein the lotion may further comprise the conventional ingredients of lotion such as abrasive, buffer, distilled water, glycerin, spice, oil and alcohol. In case of the facial cream, xanthorrizol may be included in a concentration of 0.001 to 3.0%(w/w) together with the conventional ingredients for facial cream such as abrasive, distilled water, glycerin, buffer, spice and oil.

The present invention is further illustrated in the following examples, which should not be taken to limit the scope of the invention.

EXAMPLE 1

Preparation of Crude Extract

Example 1-1
Preparation of Crude Extract Having Antibacterial Activity 100 g of *Curcuma xanthorriza* Roxb. lysate was repeatedly extracted with 400 ml of 75%(v/v) methanol at room temperature for two days. Then, the extract was filtered through Whatman filter paper(No. 2), condensed using rotary evaporator(Heidolph VV2011, Switzerland) to eliminate solvent, and freeze-dried to obtain 11.5 g of methnol extract.

The methanol extract was fractionated based on the polarity of organic solvents as following: the methanol extract was condensed to remove solvent, extracted with 4 volumes of ethylacetate twice to give 4.8 g of ethylacetate fraction. Then, 1.7 g of butanol extract was obtained by the same procedure employing butanol. Subsquently, 1.1 g of water fraction was yielded. To measure the antibacterial activity, each of the methanol fraction, ethylacetate fraction, butanol fraction and water fraction was dissolved in dimethylsulfoxide(DMSO) to give specimens in a concentration of 2%, 1% and 0.1% for each fraction.

To measure the antibacterial activity, *Streptococcus mutans*(ATCC 25175, U.S.A.) was stored on BHI(brain heart infusion, Difco Co., U.S.A.) medium containing 1.5% agar at 4° C. and subcultured at one month interval. Antibacterial activity of the specimens prepared above was measured by well diffusion assay: 5 ml of top agar medium including *Streptococcus mutans* was poured onto the solid medium prepared previously. After the top agar medium was hardened, wells were made by boring the top agar medium on its surface with a sterilized tip. Then, 0.1 ml of samples in 10% DMSO were loaded into the wells and allowed to diffuse for more than 2 hours. The solid medium in which samples are loaded were then incubated at 37° C. for 16 hours, and the antibacterial activity of each sample was compared on the basis of diameter(mm) of the clear zone surrounding the well. DMSO was used as control group, and the results are shown in Table 1.

TABLE 1

Antibacterial activity of solvent extracts

| Conc. (%) | Diameter of Clear Zone (mm) | | | |
|---|---|---|---|---|
| | Methanol Extract | Ethylacetate Fraction | Butanol Fraction | Water Fraction |
| 2 | 18 | 20 | — | — |
| 1 | 16 | 19 | — | — |
| 0.1 | 15 | 15 | — | — |

As shown in Table 1, ethylacetate fraction exhibited the highest antibacterial activity. Therefore, further purification of a single compound from the ethylacetate fraction was performed.

After eliminating solvent from the ethylacetate fraction with rotary evaporator, the remaining substances were dissolved in 10% DMSO and assayed for antibacterial activity. The specimens were prepared in a concentration of 0.001, 0.003, and 0.005%, treated with *Streptococcus mutans* at 37° C. for 1, 2, 5 and 10 minutes, respectively, and subjected to "pour plate method" by serial 10-fold dilution to count viable cell numbers of the bacteria. The viable cell numbers were compared to those of green tea extract which is well known for its preventive effect on caries. FIG. 1 is a graph showing antibacterial activity of crude extract from *Curcuma xanthorriza* Roxb. against *Streptococcus mutans* in terms of viable cell numbers, where ♦ represents DMSO, control; ■, 0.001% crude extract; ▼, 0.003% crude extract; x, 0.005% crude extract, respectively, As shown in FIG. 1, almost all bacteria were killed within one minute when the concentration of crude extract was 0.005%(50 $\mu$g/ml). Compared to conventional medicinal herb extracts whose minimum inhibitory concentrations are within the range of 200 to 1000 $\mu$g/ml the ethylacetate crude extract exhibited higher antibacterial activity.

Example 1-2

Preparation of Tooth Paste Containing Crude Extract of *Curcuma xanthorriza* Roxb.

Tooth paste was prepared to contain the crude extract obtained in Example 1-1: alkyl sodium sulfate, sucrose fatty acid ester, sodium carboxymethylcellulose and sodium chloride were dispersed in glycerin homogeneously. Then, distilled water was added to dilute the mixture, followed by the addition of sodium. The crude extract was added to the mixture in a final concentration of 5.0, 1.0, 0.1 and 0.01%, respectively, and spice was added under a vacuum condition to give cream-type tooth pastes, whose particular ingredients are disclosed in Table 2.

TABLE 2

Tooth pastes containing crude extract of *Curcuma xanthorrhiza* Roxb.

| Ingredient | Tooth Paste I | Tooth Paste II | Tooth Paste III | Tooth Paste IV |
|---|---|---|---|---|
| Crude Extract | 5.0% | 1.0% | 0.1% | 0.01% |
| Sorbitol Solution | 19.2% | 19.2% | 19.2% | 19.2% |
| Glycerin | 22.0% | 22.0% | 22.0% | 22.0% |
| Sucrose Fatty Acid Ester | 2.0% | 2.0% | 2.0% | 2.0% |
| Alkyl Sodium Sulfate | 1.7% | 1.7% | 1.7% | 1.7% |
| Sodium Chloride | 1.0% | 1.0% | 1.0% | 1.0% |
| Spice | 1.1% | 1.1% | 1.1% | 1.1% |
| Sodium Carboxymethylcellulose | 0.4% | 0.4% | 0.4% | 0.4% |
| Distilled Water | q.s. | q.s. | q.s. | q.s. |

Each of the tooth paste containing the crude extract was taken to test-tubes, dissolved in 4 ml of medium for dental pathogens, and mixed with 1 ml of dental pathogen cultures. The test-tubes were incubated with shaking, and antibacterial activity was measured by counting viable cells with the lapse of time. Similarly, the antibacterial activity of crude extract-free tooth paste as a control was also determined against the dental pathogens. The results are shown in Table 3.

TABLE 3

Antibacterial activity of tooth pastes containing crude extract of *Curcuma xanthorrhiza* Roxb.

| Dental Pathogen | Test Solution | Viable Cell Count (cell number/ml) 0 hr | 24 hr |
|---|---|---|---|
| *Streptococcus mutans* | Tooth Paste I | $2.0 \times 10^5$ | <1 |
| | Tooth Paste II | $2.0 \times 10^5$ | <1 |
| | Tooth Paste III | $2.0 \times 10^5$ | <1 |
| | Tooth Paste IV | $2.0 \times 10^5$ | <1 |
| | Control | $2.0 \times 10^5$ | $3.1 \times 10^4$ |
| *Streptococcus sobrinus* | Tooth Paste I | $9.1 \times 10^5$ | <1 |
| | Tooth Paste II | $9.1 \times 10^5$ | <1 |
| | Tooth Paste III | $9.1 \times 10^5$ | <1 |
| | Tooth Paste IV | $9.1 \times 10^5$ | <1 |
| | Control | $9.1 \times 10^5$ | $3.1 \times 10^4$ |
| *Porphyromonas gingivalis* | Tooth Paste I | $5.5 \times 10^5$ | <1 |
| | Tooth Paste II | $5.5 \times 10^5$ | <10 |
| | Tooth Paste III | $5.5 \times 10^5$ | <15 |
| | Tooth Paste IV | $5.5 \times 10^5$ | $6.7 \times 10^3$ |
| | Control | $5.5 \times 10^5$ | $3.1 \times 10^4$ |
| *Actinomyces viscosus* | Tooth Paste I | $8.2 \times 10^5$ | <1 |
| | Tooth Paste II | $8.2 \times 10^5$ | <1 |
| | Tooth Paste III | $8.2 \times 10^5$ | <1 |
| | Tooth Paste IV | $8.2 \times 10^5$ | <15 |
| | Control | $8.2 \times 10^5$ | $2.5 \times 10^4$ |

As shown in Table 3, the tooth pastes containing the crude extract exhibited higher antibacterial activity against the dental pathogens, compared to that of control which does not contain the crude extract.

Example 1-3
Preparation of Oral Cleansers Containing Crude Extract of *Curcuma xanthorrhiza* Roxb.

To prepare oral cleanser, the crude extract was first mixed with water in a concentration of 1.0, 0.1, 0.01 and 0.001%, respectively, and subsequently with citrate solution and 1-menthol dissolved in ethanol. Then, sodium saccharin and sodium fluoride were dissolved in water, and added to the said mixtures together with pigments, peppermint essence and spearmint essence. And then, to the mixtures was added water to give homogeneous mixtures with equal amounts, whose particular ingredients are disclosed in Table 4.

TABLE 4

Oral cleansers containing crude extract of *Curcuma xanthorrhiza* Roxb.

| Oral Cleanser | Oral Cleanser I | Oral Cleanser II | Oral Cleanser III | Oral Cleanser IV |
|---|---|---|---|---|
| Crude Extract | 1.0% | 0.1% | 0.01% | 0.001% |
| Sodium Fluoride | 0.02% | 0.02% | 0.02% | 0.02% |
| Ethanol | 6.6% | 6.6% | 6.6% | 6.6% |
| Glycerin | 6.0% | 6.0% | 6.0% | 6.0% |
| /-Menthol | 0.005% | 0.005% | 0.005% | 0.005% |
| Sodium Saccharin | q.s. | q.s. | q.s. | q.s. |
| Citric Acid | q.s. | q.s. | q.s. | q.s. |
| Pigment | q.s. | q.s. | q.s. | q.s. |
| Peppermint Essence | q.s. | q.s. | q.s. | q.s. |
| Spearmint Essence | q.s. | q.s. | q.s. | q.s. |

4 ml of each oral cleanser containing the crude extract with different concentrations was taken to test-tubes, and mixed with 1 ml of dental pathogen cultures. The test-tubes were incubated with shaking, and antibacterial activity was measured after 24 hours by counting viable cell numbers, whose results are shown in Table 5.

TABLE 5

Antibacterial activity of oral cleansers containing crude extract of *Curcuma xanthorrhiza* Roxb.

| Dental Pathogen | Test Solution | Viable Cell Count (cell number/ml) 0 hr | 24 hr |
|---|---|---|---|
| *Streptococcus mutans* | Oral Cleanser I | $2.0 \times 10^5$ | <1 |
| | Oral Cleanser II | $2.0 \times 10^5$ | <1 |
| | Oral Cleanser III | $2.0 \times 10^5$ | <1 |
| | Oral Cleanser IV | $2.0 \times 10^5$ | $1.1 \times 10^3$ |
| | Control | $2.0 \times 10^5$ | $2.5 \times 10^4$ |
| *Streptococcus sobrinus* | Oral Cleanser I | $9.1 \times 10^5$ | <1 |
| | Oral Cleanser II | $9.1 \times 10^5$ | <1 |
| | Oral Cleanser III | $9.1 \times 10^5$ | <1 |
| | Oral Cleanser IV | $9.1 \times 10^5$ | $2.5 \times 10^2$ |
| | Control | $9.1 \times 10^5$ | $2.5 \times 10^4$ |
| *Porphyromonas gingivalis* | Oral Cleanser I | $5.5 \times 10^5$ | <5 |
| | Oral Cleanser II | $5.5 \times 10^5$ | <15 |
| | Oral Cleanser III | $5.5 \times 10^5$ | $1.1 \times 10^2$ |
| | Oral Cleanser IV | $5.5 \times 10^5$ | $1.2 \times 10^3$ |
| | Control | $5.5 \times 10^5$ | $2.5 \times 10^4$ |
| *Actinomyces viscosus* | Oral Cleanser I | $8.2 \times 10^5$ | <1 |
| | Oral Cleanser II | $8.2 \times 10^5$ | <1 |
| | Oral Cleanser III | $8.2 \times 10^5$ | <10 |
| | Oral Cleanser IV | $8.2 \times 10^5$ | $4.5 \times 10^3$ |
| | control | $8.2 \times 10^5$ | $2.5 \times 10^4$ |

As clearly demonstrated in Table 5, oral cleansers containing crude extract of *Curcuma xanthorrhiza* Roxb. were proven to have higher antibacterial activity against the dental pathogens causing caries, compared to that of control groups.

Example 1-4
Preparation of Chewing Gum Containing Crude Extract of *Curcuma xanthorrhiza* Roxb.

Gum base, starch hydrolysate, glucose, glycerin and sugar powder were mixed in a prewarmed blender. Then, to the mixture was added the crude extract in a final concentration of 1.0, 0.1, 0.01 and 0.001%, respectively, and mixed with spice and distilled water in the blender whose inner temperature was maintained at 55° C. for 20 minutes, finally to give chewing gum. Particular ingredients of the chewing gum thus prepared are disclosed in Table 6.

TABLE 6

Chewing gum containing crude extract of *Curcuma xanthorrhiza* Roxb.

| Chewing Gum | Chewing Gum I | Chewing Gum II | Chewing Gum III | Chewing Gum IV |
|---|---|---|---|---|
| Crude Extract | 1.0% | 0.1% | 0.01% | 0.001% |
| Gum Base | 20% | 20% | 20% | 20% |
| Sugar Powder | 54% | 54% | 54% | 54% |
| Starch Hydrolysate | 10% | 10% | 10% | 10% |
| Glycerin | 5% | 5% | 5% | 5% |
| Spice | q.s. | q.s. | q.s. | q.s. |
| Distilled Water | q.s. | q.s. | q.s. | q.s. |

Example 1-5
Preparation of Facial Lotion Containing Crude Extract of *Curcuma xanthorrhiza* Roxb.

To prepare facial lotion containing crude extract of *Curcuma xanthorrhiza* Roxb., the crude extract was first mixed with water in 4 different concentrations of 5.0, 1.0, 0.1 and 0.01%, respectively, and subsequently with phosphate solution. Then, ethanol, glycerin and propyleneglycol were added to the said mixtures together with spices and preservatives. And then, to the mixtures was added water to give homogeneous mixtures with equal amounts, whose particular ingredients are disclosed in Table 7.

TABLE 7

Facial lotion containing crude extract of *Curcuma xanthorrhiza* Roxb.

| Facial Lotion | Lotion I | Lotion II | Lotion III | Lotion IV |
|---|---|---|---|---|
| Crude extract | 5.0% | 1.0% | 0.1% | 0.01% |
| Glycerin | 2.0% | 2.0% | 2.0% | 2.0% |
| Propyleneglycol | 2.0% | 2.0% | 2.0% | 2.0% |
| Potassium phosphate | 0.1% | 0.1% | 0.1% | 0.1% |
| Disodium phosphate | 0.05% | 0.05% | 0.05% | 0.05% |
| Spice | 0.02% | 0.02% | 0.02% | 0.02% |
| 96% ethanol | 20% | 20% | 20% | 20% |
| Distilled water | q.s. | q.s. | q.s. | q.s. |
| Preservative | q.s. | q.s. | q.s. | q.s. |

4 ml of each facial lotion containing the crude extract was taken to test-tubes, and mixed with 1 ml of acne-causing pathogen cultures. The test-tubes were incubated with shaking, and antibacterial activity was measured after 24 hours by counting viable cell numbers, whose results are shown in Table 8.

TABLE 8

Antibacterial activity of facial lotion containing crude extract of *Curcuma xanthorrhiza* Roxb.

| Acne-causing Pathogen | Test Solution | Viable Cell Count (cell number/ml) 0 hr | 24 hr |
|---|---|---|---|
| *Propionibacterium acnes* | Lotion I | $3.0 \times 10^5$ | <1 |
| | Lotion II | $3.0 \times 10^5$ | <1 |
| | Lotion III | $3.0 \times 10^5$ | <1 |
| | Lotion IV | $3.0 \times 10^5$ | $1.1 \times 10^2$ |
| | Control | $3.0 \times 10^5$ | $3.1 \times 10^3$ |
| *Staphylococcus aureus* | Lotion I | $4.5 \times 10^5$ | <1 |
| | Lotion II | $4.5 \times 10^5$ | <1 |
| | Lotion III | $4.5 \times 10^5$ | <1 |
| | Lotion IV | $4.5 \times 10^5$ | $4.1 \times 10^2$ |
| | Control | $4.5 \times 10^5$ | $4.7 \times 10^3$ |
| *Staphlococcus epidermis* | Lotion I | $6.8 \times 10^5$ | <1 |
| | Lotion II | $6.8 \times 10^5$ | <1 |
| | Lotion III | $6.8 \times 10^5$ | <1 |
| | Lotion IV | $6.8 \times 10^5$ | $4.4 \times 10^2$ |
| | Control | $6.8 \times 10^5$ | $5.1 \times 10^3$ |

As clearly demonstrated in Table 3, facial lotion containing crude extract of *Curcuma xanthorrhiza* Roxb. was proven to have higher antibacterial activity, compared to that of control groups.

Example 1-6

Preparation of Facial Cream Containing Crude Extract of *Curcuma xanthorrhiza* Roxb.

Facial creams containing the crude extract were prepared in accordance with the components and composition ratios shown in Table 9 below: first, substances B and C were each melted down at the temperature of 75 to 80° C., followed by emulsification of the melted substance C in the melted substance B. Then, xanthorrizol was added to the mixtures in a concentration of 10.0, 1.0, 0.1 and 0.01%, respectively. Finally, spice was added to the mixtures which were adjusted to the final volume with distilled water.

TABLE 9

Facial creams containing crude extract of *Curcuma xanthorrhiza* Roxb.

| Facial Cream | Facial Cream I | Facial Cream II | Facial Cream III | Facial Cream IV |
|---|---|---|---|---|
| A | | | | |
| Crude Extract | 10.0% | 1.0% | 0.1% | 0.01% |
| Glycerin | 2.0% | 2.0% | 2.0% | 2.0% |
| Propyleneglycol | 2.0% | 2.0% | 2.0% | 2.0% |
| B | | | | |
| Chlorolauryl Sulfate | 8.0% | 8.0% | 8.0% | 8.0% |
| Stearin | 5.4% | 5.4% | 5.4% | 5.4% |
| Mineral Oil | 4.5% | 4.5% | 4.5% | 4.5% |
| C | | | | |
| Spice | 0.02% | 0.02% | 0.02% | 0.02% |
| Cetyl Alcohol | 6.5% | 6.5% | 6.5% | 6.5% |
| Distilled Water | q.s. | q.s. | q.s. | q.s. |
| Preservative | q.s. | q.s. | q.s. | q.s. |

4 ml of each cream containing the crude extract was taken to test-tubes, and mixed with 1 ml of acne-causing pathogen cultures. The test-tubes were incubated with shaking, and antibacterial activity was measured after 24 hours by counting viable cell numbers, whose results are shown in Table 10.

TABLE 10

Antibacterial activity of facial creams containing crude extract of *Curcuma xanthorrhiza* Roxb.

| Acne-causing Pathogen | Test Solution | Viable Cell Count (cell number/ml) 0 hr | 24 hr |
|---|---|---|---|
| *Propionibacterium acnes* | Facial Cream I | $3.0 \times 10^5$ | <1 |
| | Facial Cream II | $3.0 \times 10^5$ | <1 |
| | Facial Cream III | $3.0 \times 10^5$ | <1 |
| | Facial Cream IV | $3.0 \times 10^5$ | $1.3 \times 10^2$ |
| | Control | $3.0 \times 10^5$ | $3.3 \times 10^3$ |
| *Staphylococcus aureus* | Facial Cream I | $4.5 \times 10^5$ | <1 |
| | Facial Cream II | $4.5 \times 10^5$ | <1 |
| | Facial Cream III | $4.5 \times 10^5$ | <1 |
| | Facial Cream IV | $4.5 \times 10^5$ | $3.7 \times 10^4$ |
| | Control | $4.5 \times 10^5$ | $4.1 \times 10^3$ |
| *Staphlococcus epidermis* | Facial Cream I | $6.8 \times 10^5$ | <1 |
| | Facial Cream II | $6.8 \times 10^5$ | <1 |
| | Facial Cream III | $6.8 \times 10^5$ | <1 |
| | Facial Cream IV | $6.8 \times 10^5$ | $4.3 \times 10^2$ |
| | Control | $6.8 \times 10^5$ | $5.1 \times 10^3$ |

As clearly demonstrated in Table 10, facial creams containing crude extract of *Curcuma xanthorrhiza* Roxb. were proven to have higher antibacterial activity against acne-causing pathogens, compared to that of control groups.

EXAMPLE 2

Isolation and Purification of Xanthorrizol Having Antibacterial Activity

The crude extract, prepared in Example 1-1 was applied to a silica gel column chromatography: the crude extract was applied to a column chromatography(5×43 cm) filled with silica gel(Merck, U.S.A.) of 70 to 230 mesh, and eluted with a mixed gradient of hexane and ethylacetate (10:1→3:1→1:1). Then, thin layer chromatography(TLC)

was performed with the active fractions obtained in the course of chromatographic procedure to give 8 different fractions(fractions I to VIII ) with similar retention on the TLC plate. Antibacterial activity of the fractions was measured in terms of minimum inhibitory concentration(MIC), and compared to that of vancomycin. The results are shown in Table 11.

TABLE 11

Minimum inhibitory concentration of active fractions

| Fraction | MIC ($\mu$g/ml) |
|---|---|
| Fraction I | 250 |
| Fraction II | 7 |
| Fraction III | 62 |
| Fraction IV | 125 |
| Fraction V | 250 |
| Fraction VI | 250 |
| Fraction VII | No inhibitory action |
| Fraction VIII | No inhibitory action |
| Vancomycin | 1 |

Fraction II which possesses the strongest antibacterial activity was pooled to isolate substances having antibacterial activity. Since fraction II had some impurities, acetylation of the fraction was carried out to change its polarity as a procedure to obtain a single compound with antibacterial activity: 0.5 g of fraction II was dissolved in 5 ml pyridine, added with 5 ml of acetic anhydride in a drop-wise manner at ice-cold temperature, and stirred at room temperature for more than 15 hours. The reactant was subjected to partition extraction with 100 ml of ice-cold water once, and subsequently 100 ml of ethylacetate twice. The ethylacetate phase thus obtained was washed with 5% HCl, NaHCO$_3$ and NaCl, dehydrated with anhydrous MgSO$_4$, filtered and condensed under a reduced pressure. The resultant was finally applied onto a silica gel column(4.7×50 cm), and eluted with a solvent mixture of hexane and ethylacetate(15:1, v/v) to give an acetylated single compound. Since the single compound showed no antibacterial activity in its acetylated form, deacetylation was performed by dissolving the acetylated single compound in 20 ml of methanol. Then, 2 ml of 5% KOH was added to the compound, reacted with stirring for more than 2 hours, and neutralized using cation exchange resin(DOWEX50WX4-400), followed by filtration and condensation to give a single isolated compound. Thereafter, its molecular weight was measured with EI-MS(VG Platform II, FISIONS, 15 eV), and chemical identification was conducted using analytical instruments of $^1$H-NMR, $^{13}$C-NMR (400 MHz, CDCl$_3$) and IR(Perkin Elmer spectrum I , DTGS detector). The results of the analyses were as follows: IR (CDCl$_3$, v, max) 3402, 2915, 1708, 1620, 1599 cm$^{-1}$; EI-MS(m/z) 218, 148, 136, 135, 121; $^1$H-NMR(CDCl$_3$, 400 MHz): 1.18(3H, d, J=7.1 Hz, H-15), 1.52(3H, s, H-13), 1.57(2H, dt, J=7.1, 7.2 Hz, H-8), 1.67(3H, s, H-12), 1.85 (2H, dt, J=7.0, 7.2 Hz, H-9), 2.20(3H, s, H-14), 2.59(1H, qt, J=7.1, 7.1 Hz, H-7), 5.08(1H, t, J=7.0 Hz, H-10), 6.59(1H, br s, H-2), 6.66(1H, br d, J=7.6 Hz, H-6), 7.01(1H, d, J=7.6 Hz, H-5); $^{13}$C-NMR(CDCl$_3$, 400 MHz): 147.16(s, C-1), 113.50(d, C-2), 153.51(s, C-3), 120.86(s, C-4), 130.74(d, C-5), 119.42(d, C-6), 38.98(d, C-7), 38.32(t, C-8), 26.10(t, C-9), 124.48(d, C-10), 131.39(s, C-11), 15.31(q, C-12), 25.67(q, C-13), 17.64(q, C-14), 22.34(q, C-15). The $^1$H-NMR spectrum showed 2- or 3-substituted hydroxy-α-curcumene from its aromatic proton signal. Also, through the analysis of chemical shift of $^{13}$C-NMR signal, the compound was found to have 1,3,4-substituted benzene ring system. Taken together, the compound was identified as xanthorrizol(1,3,5,10-bisabolatetraen-3-ol), a sequiterpenoid having bisabolane structure, which is colorless oily material having the optical rotation of [α]=−50.2°(C=0.65, CHCl$_3$).

EXAMPLE 3

Heat Stability and Antibacterial Activity of Xanthorrizol

Example 3-1

Antibacterial Activity of Xanthorrizol

Figure 2:
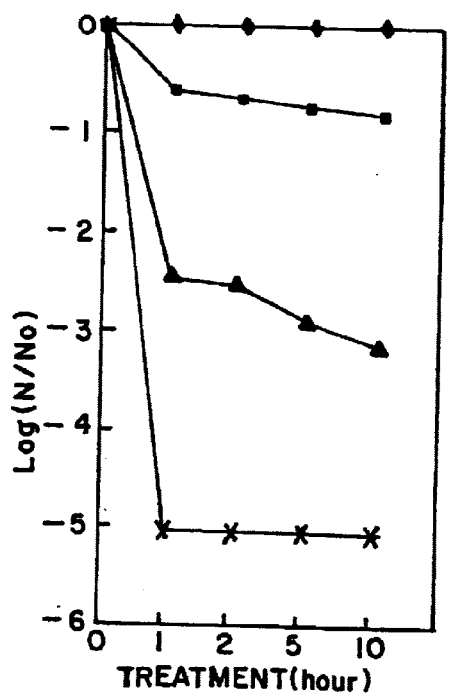
FIG. 2 is a graph showing antibacterial activity of purified xanthorrizol against Propionibacterium acnes in terms of viable cell count.

To measure the antibacterial activity of xanthorrizol, it was dissolved in DMSO to give specimens with a concentration of 0.001%, 0.0015% and 0.002%, respectively, and incubated with test microorganisms(2×10 CFU/ml) at 37° C. for 1, 2, 5, and 10 hours, respectively. Then, they were subjected to serial 10-fold dilution, incubated with an acne-causing pathogen, *Propionibacterium acnes* for 24 to 48 hours, and counted the viable cell number of the pathogen. FIG. 2 is a graph showing antibacterial activity of xanthorrizol in terms of viable cell numbers, where ♦ represents DMSO, control; ■, 0.001% crude extract; ▼, 0.0015% crude extract; x, 0.002% crude extract, respectively. As clearly demonstrated in FIG. 2, the microorganism was eradicated almost completely in one hour at the concentration of xanthorrizol of 0.002%, indicating that xanthorrizol exerts strong antibacterial activity against *Propionibacterium acnes* at low concentrations.

Figure 3:
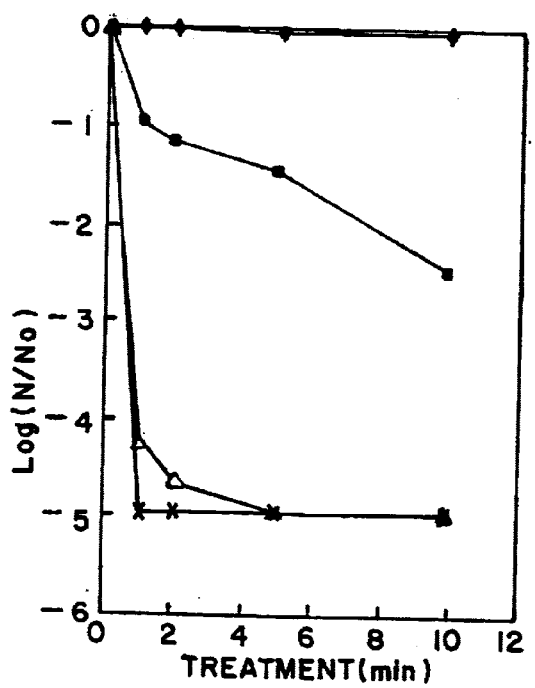
FIG. 3 is a graph showing antibacterial activity of purified xanthorrizol against *Streptococcus mutans* using viable cell count.

Xanthorrizol was also tested for *Streptococcus mutans* in a similar manner as described above: xanthorrizol was dissolved in DMSO to give specimens with a concentration of 0.0002%, 0.0004% and 0.0008%, respectively. Then, the specimens were incubated with the microorganism at 37° C. for 1, 2, 5 and 10 minutes, respectively, and subjected to serial 10-fold dilution. After the incubation with the pathogen, viable cell number for Streptococcus mutans was counted. FIG. 3 is a graph showing antibacterial activity of xanthorrizol against Streptococcus mutans in terms of viable cell number, where ♦ represents DMSO, control; ■, 0.0002% crude extract; Δ, 0.0004% crude extract; x, 0.0008% crude extract, respectively. As shown in FIG. 3, the microorganism was eradicated almost completely in one minute at the concentration of xanthorrizol of 0.0004%(4 $\mu$g/ml), demonstrating that xanthorrizol exhibits strong antibacterial activity against *Streptococcus mutans* at low concentrations.

In addition, minimum inhibitory concentration(MIC, $\mu$g/ml) for various microorganisms was determined by performing 2-fold dilution: first, 1 ml of medium was taken into each tube, and 1 ml of xanthorrizol(0.05% in DMSO) was added to only one tube to make 2-fold dilution. Then, serial 2-fold dilution was further carried out for the rest of the tubes, starting from the tube containing xanthorrizol. 100 $\mu$l of microorganism was added into each tube prepared by the 2-fold dilution to contain a final cell number of 2×10$^5$ CFU/ml, and incubated at 30 to 37° C. for more than 24 hours to determine minimum inhibitory concentrations for various test microorganisms(see: Table 12).

TABLE 12

Minimum inhibitory concentration (MIC, μg/ml) of xanthorrizol over various test microorganisms

| Microorganism | MIC | Microorganism | MIC |
|---|---|---|---|
| Actinomyces viscosus ATCC 15988 | 16 | Pityrosporum pacchydermatis ATCC 14522 | 125 |
| Bifidobacterium bifidum ATCC 29521 | 250 | Porphyromonas gingivalis W 50 | 32 |
| Candida albicans ATCC 10231 | 125 | Propionibacterium acnes ATCC 6919 | 16 |
| Candida glabrata IFO 0622 | 125 | Saccharomyces cerevisiae ATCC 9763 | 250 |
| Cladosporium cladosporioides IFO 6348 | 500 | Salmonella typhimurium IFO 12529 | 62.5 |
| Enterococcus faecalis ATCC 19433 | 16 | Staphylococcus aureus ATCC 12600 | 62.5 |
| Lactobacillus casei ATCC 4646 | 250 | Streptococcus mutans ATCC 25175 | 2 |
| Lactobacillus aciophilus ATCC 4356 | 500 | Streptococcus sobrinus ATCC 27351 | 4 |
| Penicilium chrysogenum IFO 5472 | 125 | Streptococcus salivarius ATCC 9758 | 4 |
| Penicilium citrinum IFO 6352 | 250 | Streptococcus sanguis ATCC 35105 | 4 |
|  |  | Streptomyces bikiniensis ATCC 11062 | 32 |

As shown in Table 12, it was clearly demonstrated that xanthorrizol shows a broad spectrum of antibacterial activity.

Example 3-2
Thermal Stability of Xanthorrizol

Xanthorrizol was dissolved in DMSO to prepare specimens with a concentration of 0.1%. The specimens were heated for 30 minutes at the temperature of 60° C., 70° C., 80° C., 90° C., 100° C. and 121° C., respectively. Then, antibacterial activity against Streptococcus mutans was determined for each specimen by well diffusion analysis, whose results are shown in Table 13.

TABLE 13

Antibacterial activity of xanthorrizol at various temperatures

| Treatment Temp. (° C.) | 60 | 70 | 80 | 90 | 100 | 121 |
|---|---|---|---|---|---|---|
| Diameter of Clear Zone (mm) | 17 | 16 | 17 | 17 | 18 | 17 |

As shown in Table 13, it was clearly demonstrated that xanthorrizol has a strong antibacterial activity even under a high temperature of 60 to 121° C.

Figure 4A:
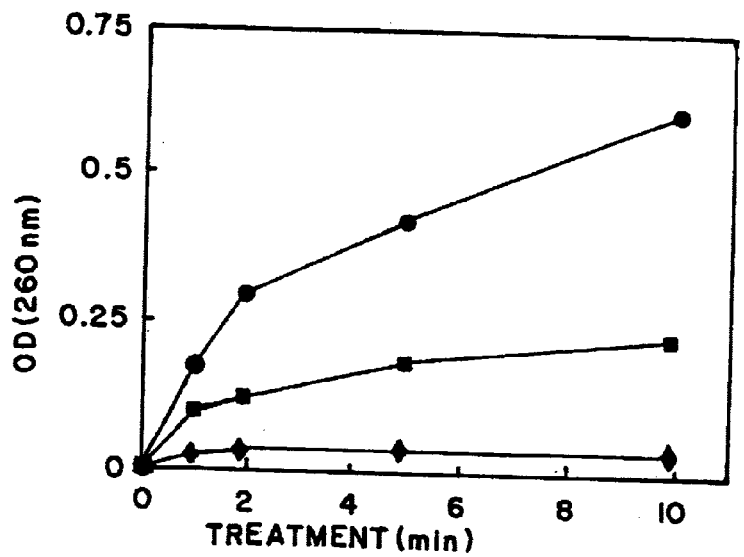
FIG. 4a is a graph showing the absorbance change by the efflux of nucleic acid from *Streptococcus mutans* after xanthorrizol treatment.
Figure 4B:
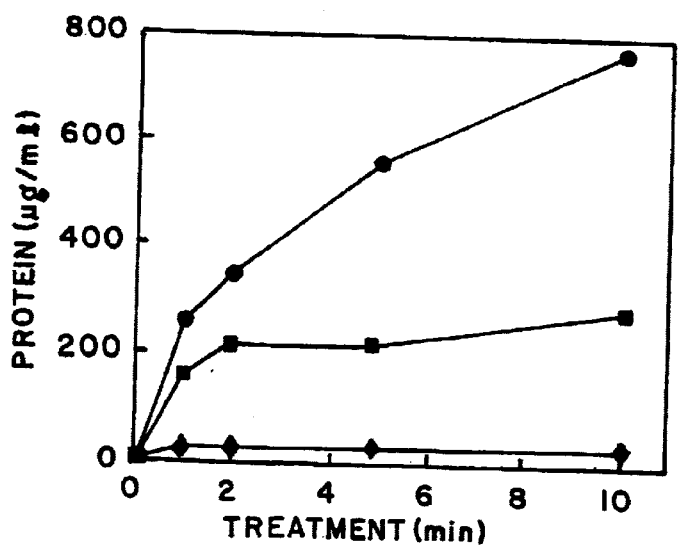
FIG. 4b is a graph showing the absorbance change by the efflux of protein from *Streptococcus mutans* after xanthorrizol treatment.
Figure 5A:
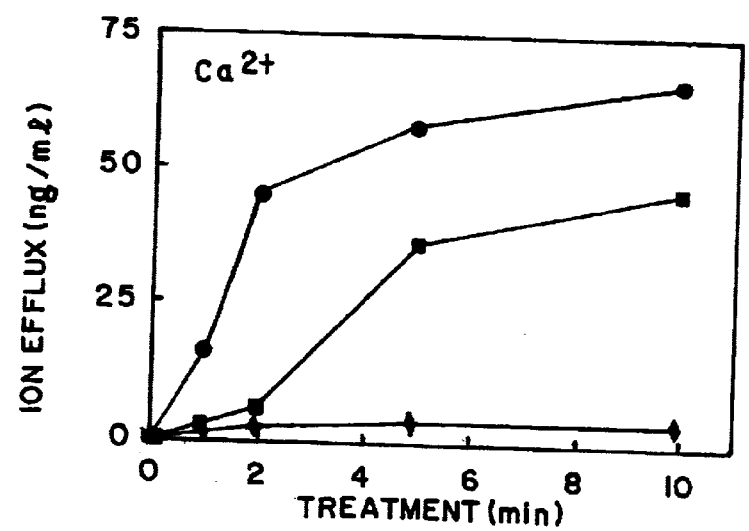
FIG. 5a is a graph showing the absorbance change by the efflux of calcium from *Streptococcus mutans* after xanthorrizol treatment.
Figure 5B:
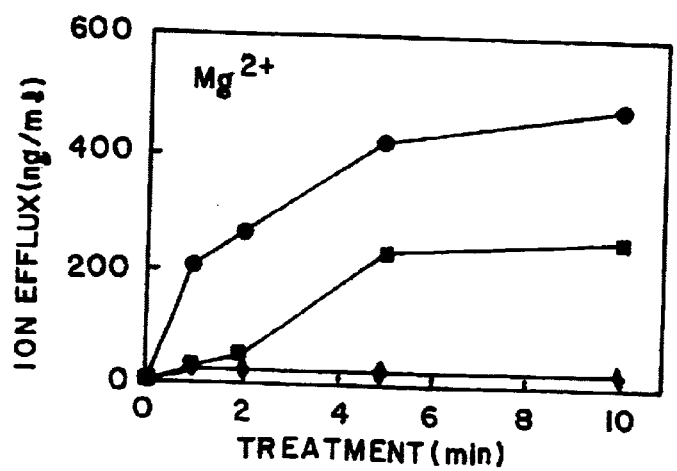
FIG. 5b is a graph showing absorbance change by the efflux of magnesium from *Streptococcus mutans* after xanthorrizol treatment.

Example 3-3
Efflux of Intracellular Macromolecules and Ions After Xanthorrizol Treatment Streptococcus mutans was treated with 5 and 10 μg/ml of xanthorrizol for 1, 2, 5 and 10 minutes, respectively, to examine the efflux of intracellular macromolecules and ions by the xanthorrizol-mediated cell damage. FIGS. 4a and 4b are graphs showing the efflux of neucleic acid and protein from Streptococcus mutans after xanthorrizol treatment, and FIGS. 5a and 5b, calcium efflux and magnesium efflux, where ♦ represents 0.1% DMSO, control; ■, Streptococcus mutans treated with 5 μg/ml xanthorrizol; •, Streptococcus mutans treated with 10 μg/ml xanthorrizol, respectively.

As shown in FIGS. 4a, 4b, 5a and 5b, it was clearly demonstrated that the efflux of protein, neucleic acid and ion was increased dramatically in 5 minutes after the treatment of xanthorrizol, and more efflux was detected in a group treated with 10 μg/ml xanthorrixol than a group treated with 5 μg/ml xanthorrizol. Given that the efflux of intracellular macromolecules and ions was detected in the presence of 5 μg/ml xanthorrizol, it could be appreciated that the overall experimental data were consistent in a sense that antibacterial activity against Streptococcus mutans was also observed under the treatment of 5 μg/ml xanthorrizol.

Example 3-4
Change in Cell Morphology After Xanthorrizol Treatment

To assess the extent of xanthorrizol-mediated cell damage, 10 μg/ml xanthorrizol was treated to the pathogens for 30 minutes. Then, cell morphology was observed with transmission electron microscope (TEM). In cells treated with xanthorrizol, cell wall expansion was detected, followed by cell disruption accompanying the efflux of intracelluar macromolecules from the cells. These results suggested that xanthorrizol-mediated cell wall or cell membrane damage caused the disruption in osmotic balance and physiological conditions, leading to cell death. Further, it was assumed that through the efflux of intracellular macromolecules and ions, the permeability of cell wall is increased to accelerate the efflux of intracellular components, which in turn inactivates cellular enzymes and causes the malfunction of cell wall.

EXAMPLE 4

Preparation of Tooth Paste Containing Xanthorrizol

Tooth paste containing xanthorrizol was prepared as following: first, alkyl sodium sulfate, sucrose fatty acid ester, sodium carboxymethylcellulose and. sodium chloride were dispersed in glycerin homogeneously. Then, distilled water was added to dilute the mixture, followed by the addition of sodium. Then, xanthorrizol was added to the mixture in a final concentration of 1.0, 0.1, 0.01 and 0.001%, respectively, and spice was further added under a vacuum condition to give cream-type tooth pastes, whose ingredients are disclosed in Table 14.

TABLE 14

Tooth pastes containing xanthorrizol

| Ingredient | Tooth Paste I | Tooth Paste II | Tooth Paste III | Tooth Paste IV |
|---|---|---|---|---|
| Xanthorrizol | 1.0% | 0.1% | 0.01% | 0.001% |
| Sorbitol Solution | 19.2% | 19.2% | 19.2% | 19.2% |
| Glycerin | 22.0% | 22.0% | 22.0% | 22.0% |
| Sucrose Fatty Acid Ester | 2.0% | 2.0% | 2.0% | 2.0% |
| Alkyl Sodium Sulfate | 1.7% | 1.7% | 1.7% | 1.7% |
| Sodium Chloride | 1.0% | 1.0% | 1.0% | 1.0% |
| Spice | 1.1% | 1.1% | 1.1% | 1.1% |
| Sodium Carboxymethylcellulose | 0.4% | 0.4% | 0.4% | 0.4% |
| Distilled Water | q.s. | q.s. | q.s. | q.s. |

4 ml of each tooth paste containing xanthorrizol was taken to test-tubes, and mixed with 1 ml of dental pathogen cultures. The test-tubes were incubated with shaking, and antibacterial activity was measured by counting viable cells with the lapse of time. Similarly, antibacterial activity of xanthorrizol-free tooth paste as a control was also determined against the dental pathogens. The results is are shown in Table 15.

TABLE 15

Antibacterial activity of tooth pastes containing xanthorrizol

| Dental Pathogen | Test Solution | Viable Cell Count (cell number/ml) | |
|---|---|---|---|
| | | 0 hr | 24 hr |
| Streptococcus mutans | Tooth Paste I | $2.0 \times 10^5$ | <1 |
| | Tooth Paste II | $2.0 \times 10^5$ | <1 |
| | Tooth Paste III | $2.0 \times 10^5$ | <1 |
| | Tooth Paste IV | $2.0 \times 10^5$ | <1 |
| | Control | $2.0 \times 10^5$ | $3.1 \times 10^2$ |
| Streptococcus sobrinus | Tooth Paste I | $9.1 \times 10^5$ | <1 |
| | Tooth Paste II | $9.1 \times 10^5$ | <1 |
| | Tooth Paste III | $9.1 \times 10^5$ | <1 |
| | Tooth Paste IV | $9.1 \times 10^5$ | <1 |
| | Control | $9.1 \times 10^5$ | $3.1 \times 10^2$ |
| Porphyromonas gingivalis | Tooth Paste I | $5.5 \times 10^5$ | <1 |
| | Tooth Paste II | $5.5 \times 10^5$ | <5 |
| | Tooth Paste III | $5.5 \times 10^5$ | $3.1 \times 10^2$ |
| | Tooth Paste IV | $5.5 \times 10^5$ | $2.1 \times 10^3$ |
| | Control | $5.5 \times 10^5$ | $3.1 \times 10^4$ |
| Actinomyces viscosus | Tooth Paste I | $8.2 \times 10^5$ | <1 |
| | Tooth Paste II | $8.2 \times 10^5$ | <1 |
| | Tooth Paste III | $8.2 \times 10^5$ | <10 |
| | Tooth Paste IV | $8.2 \times 10^5$ | $2.0 \times 10^2$ |
| | Control | $8.2 \times 10^5$ | $3.1 \times 10^4$ |

As clearly shown in Table 15, the tooth paste containing xanthorrizol exhibited higher antibacterial activity against the dental pathogens, compared to that of control which does not contain xanthorrizol.

EXAMPLE 5

Preparation of Oral Cleansers Containing Xanthorrizol

Several kinds of oral cleansers were prepared by the conventional method to contain xanthorrizol in a concentration of 0.1%, 0.01%, 0.001% and 0.0001%, respectively, whose components and composition ratios are disclosed in Table 16.

TABLE 16

Oral cleansers containing xanthorrizol

| Oral Cleanser | Oral Cleanser I | Oral Cleanser II | Oral Cleanser III | Oral Cleanser IV |
|---|---|---|---|---|
| Xanthorrizol | 0.1% | 0.01% | 0.001% | 0.0001% |
| Sodium Fluoride | 0.02% | 0.02% | 0.02% | 0.02% |
| Ethanol | 6.6% | 6.6% | 6.6% | 6.6% |
| Glycerin | 6.0% | 6.0% | 6.0% | 6.0% |
| /-menthol | 0.005% | 0.005% | 0.005% | 0.005% |
| Sodium Saccharin | q.s. | q.s. | q.s. | q.s. |
| Citric Acid | q.s. | q.s. | q.s. | q.s. |
| Pigment | q.s. | q.s. | q.s. | q.s. |
| Peppermint Essence | q.s. | q.s. | q.s. | q.s. |
| Spearmint Essence | q.s. | q.s. | q.s. | q.s. |

4 ml of each oral cleanser containing xanthorrizol with different concentrations was taken to test-tubes, and mixed with 1 ml of dental pathogen cultures. The test-tubes were incubated with shaking, and antibacterial activity was measured with the lapse of time by counting viable cell numbers, whose results are shown in Table 17.

TABLE 17

Antibacterial activity of oral cleansers containing xanthorrizol

| Dental Pathogen | Test Solution | Viable Cell Count (cell number/ml) | |
|---|---|---|---|
| | | 0 hr | 24 hr |
| Streptococcus mutans | Oral cleanser I | $2.0 \times 10^5$ | <1 |
| | Oral cleanser II | $2.0 \times 10^5$ | <1 |
| | Oral cleanser III | $2.0 \times 10^5$ | <1 |
| | Oral cleanser IV | $2.0 \times 10^5$ | $3.2 \times 10^2$ |
| | Control | $2.0 \times 10^5$ | $2.5 \times 10^4$ |
| Streptococcus sobrinus | Oral cleanser I | $9.1 \times 10^5$ | <1 |
| | Oral cleanser II | $9.1 \times 10^5$ | <1 |
| | Oral cleanser III | $9.1 \times 10^5$ | <1 |
| | Oral cleanser IV | $9.1 \times 10^5$ | $1.1 \times 10^2$ |
| | Control | $9.1 \times 10^5$ | $2.5 \times 10^4$ |
| Porphyromonas gingivalis | Oral cleanser I | $5.5 \times 10^5$ | <5 |
| | Oral cleanser II | $5.5 \times 10^5$ | <10 |
| | Oral cleanser III | $5.5 \times 10^5$ | $1.7 \times 10^2$ |
| | Oral cleanser IV | $5.5 \times 10^5$ | $5.5 \times 10^3$ |
| | Control | $5.5 \times 10^5$ | $2.5 \times 10^4$ |
| Actinomyces viscosus | Oral cleanser I | $8.2 \times 10^5$ | <1 |
| | Oral cleanser II | $8.2 \times 10^5$ | <1 |
| | Oral cleanser III | $8.2 \times 10^5$ | $1.2 \times 10^2$ |
| | Oral cleanser IV | $8.2 \times 10^5$ | $1.1 \times 10^3$ |
| | Control | $8.2 \times 10^5$ | $2.5 \times 10^4$ |

As shown in Table 17, oral cleansers containing xanthorrizol were proven to have higher antibacterial activity on dental pathogens causing caries than control group.

EXAMPLE 6

Preparation of Chewing Gum Containing Xanthorrizol

Gum base, starch hydrolysate, glucose, glycerin and sugar powder were mixed in a prewarmed blender. Then, to the mixture was added xanthorrizol in a final concentration of 0.1, 0.01, 0.001 and 0.0001%, respectively, and mixed with spice and distilled water in the blender whose inner temperature was maintained at 55° C. for 20 minutes, finally to give chewing gum. The ingredients of the chewing gum thus prepared are shown in Table 18.

TABLE 18

Chewing gum containing xanthorrizol

| Chewing Gum | Chewing Gum I | Chewing Gum II | Chewing Gum III | Chewing Gum IV |
|---|---|---|---|---|
| Xanthorrizol | 0.1% | 0.01% | 0.001% | 0.0001% |
| Gum Base | 20% | 20% | 20% | 20% |
| Sugar Powder | 54% | 54% | 54% | 54% |
| Starch Hydrolysate | 10% | 10% | 10% | 10% |
| Glycerin | 5% | 5% | 5% | 5% |
| Spice | q.s. | q.s. | q.s. | q.s. |
| Distilled Water | q.s. | q.s. | q.s. | q.s. |

EXAMPLE 7

Preparation of Antibacterial Soap Containing Xanthorrizol

Xanthorrizol was mixed with soap base to a final concentration of 0.001%, 0.01%, 0.1%, 1.0% and 5.0%(w/w), respectively. In accordance with the conventional method, antibacterial soap was prepared by adding spice and pigment to the mixture. Table 19 discloses the ingredients of antibacterial soap.

TABLE 19

Antibacterial soap containing xanthorrizol

| Antibacterial Soap | Soap I | Soap II | Soap III | Soap IV | Soap V |
|---|---|---|---|---|---|
| Xanthorrizol | 0.001% | 0.01% | 0.1% | 1.0% | 5.0% |
| Soap Base | q.s. | q.s. | q.s. | q.s. | q.s. |
| Spice | q.s. | q.s. | q.s. | q.s. | q.s. |
| Pigment | q.s. | q.s. | q.s. | q.s. | q.s. |

Each antibacterial soap containing xanthorrizol with different concentrations was taken to 4 ml of medium, and mixed with 1 ml of skin infectious pathogen cultures. The test-tubes were incubated with shaking, and antibacterial activity was measured after 48 hour by counting viable cells. As a control, antibacterial activity of xanthorrizol-free soap was also examined in an analogous manner. The results are disclosed in Table 20.

TABLE 20

Antibacterial activity of soap containing xanthorrizol

| Acne-causing Pathogen | Test Solution | Viable Cell Count (cell number/ml) 0 hr | 24 hr |
|---|---|---|---|
| *Propionibacterium acnes* | Soap I | $2.0 \times 10^5$ | $1.2 \times 10^4$ |
| | Soap II | $2.0 \times 10^5$ | <10 |
| | Soap III | $2.0 \times 10^5$ | <1 |
| | Soap IV | $2.0 \times 10^5$ | <1 |
| | Soap V | $2.0 \times 10^5$ | <1 |
| | Control | $2.0 \times 10^5$ | $4.3 \times 10^3$ |
| *Candida albicans* | Soap I | $4.4 \times 10^5$ | $5.1 \times 10^3$ |
| | Soap II | $4.4 \times 10^5$ | <20 |
| | Soap III | $4.4 \times 10^5$ | <1 |
| | Soap IV | $4.4 \times 10^5$ | <1 |
| | Soap V | $4.4 \times 10^5$ | <1 |
| | Control | $4.4 \times 10^5$ | $4.1 \times 10^2$ |
| *Staphylococcus aureus* | Soap I | $4.2 \times 10^5$ | $2.3 \times 10^4$ |
| | Soap II | $4.2 \times 10^5$ | <10 |
| | Soap III | $4.2 \times 10^5$ | <1 |
| | Soap IV | $4.2 \times 10^5$ | <1 |
| | Soap V | $4.2 \times 10^5$ | <1 |
| | Control | $4.2 \times 10^5$ | $4.5 \times 10^5$ |
| *Staphylococcus epidermis* | Soap I | $5.8 \times 10^5$ | $1.2 \times 10^4$ |
| | Soap II | $5.8 \times 10^5$ | <15 |
| | Soap III | $5.8 \times 10^5$ | <1 |
| | Soap IV | $5.8 \times 10^5$ | <1 |
| | Soap V | $5.8 \times 10^5$ | <1 |
| | Control | $5.8 \times 10^5$ | $6.2 \times 10^5$ |

As shown in Table 20, soap containing xanthorrizol exerted stronger antibacterial effects on skin infectious pathogens than control.

EXAMPLE 8

Preparation of Facial Lotion Containing Xanthorrizol

To prepare facial lotion of the invention, xanthorrizol was first mixed with water in 4 different concentrations of 1.0, 0.1, 0.01 and 0.001%, respectively, and subsequently with phosphate solution. Then, ethanol, glycerin and propyleneglycol were added to the said mixtures together with spices and preservatives. And then, to the mixtures was added water to give homogeneous mixtures with equal amounts, whose particular ingredients are disclosed in Table 21.

TABLE 21

Facial lotion containing xanthorrizol

| Facial Lotion | Lotion I | Lotion II | Lotion III | Lotion IV |
|---|---|---|---|---|
| Xanthorrizol | 1.0% | 0.1% | 0.01% | 0.001% |
| Glycerin | 2.0% | 2.0% | 2.0% | 2.0% |
| Propyleneglycol | 2.0% | 2.0% | 2.0% | 2.0% |
| Calcium Phosphate | 1.0% | 1.0% | 1.0% | 1.0% |
| Disodium Phosphate | 0.05% | 0.05% | 0.05% | 0.05% |
| Spice | 0.02% | 0.02% | 0.02% | 0.02% |
| 96% Ethanol | 50% | 50% | 50% | 50% |
| Distilled Water | q.s. | q.s. | q.s. | q.s. |
| Preservative | q.s. | q.s. | q.s. | q.s. |

4 ml of each facial lotion containing xanthorrizol was taken to test-tubes, and mixed with 1 ml of acne-causing pathogen cultures. The test-tubes were incubated with shaking, and antibacterial activity was measured after 24 hours by counting viable cell numbers, whose results are shown in Table 22.

TABLE 22

Antibacterial activity of facial lotion containing xanthorrizol

| Acne-causing Pathogen | Test Solution | Viable Cell Count (cell number/ml) 0 hr | 24 hr |
|---|---|---|---|
| *Propionibacterium acnes* | Lotion I | $3.0 \times 10^5$ | <1 |
| | Lotion II | $3.0 \times 10^5$ | <1 |
| | Lotion III | $3.0 \times 10^5$ | <1 |
| | Lotion IV | $3.0 \times 10^5$ | $1.2 \times 10^2$ |
| | Control | $3.0 \times 10^5$ | $3.1 \times 10^3$ |
| *Staphylococcus aureus* | Lotion I | $4.5 \times 10^5$ | <1 |
| | Lotion II | $4.5 \times 10^5$ | <1 |
| | Lotion III | $4.5 \times 10^5$ | <1 |
| | Lotion IV | $4.5 \times 10^5$ | $3.1 \times 10^2$ |
| | Control | $4.5 \times 10^5$ | $4.7 \times 10^3$ |
| *Staphylococcus epidermis* | Lotion I | $6.8 \times 10^5$ | <1 |
| | Lotion II | $6.8 \times 10^5$ | <1 |
| | Lotion III | $6.8 \times 10^5$ | <1 |
| | Lotion IV | $6.8 \times 10^5$ | $3.5 \times 10^2$ |
| | Control | $6.8 \times 10^5$ | $5.1 \times 10^2$ |

As clearly demonstrated in Table 22, facial lotion containing xanthorrizol was proven to have higher antibacterial activity against acne-causing pathogens, compared to that of control groups.

EXAMPLE 9

Preparation of Facial Cream Containing Xanthorrizol

Facial creams containing xanthorrizol were prepared in accordance with the components and composition ratios shown in Table 23: first, substances B and C were each melted down at the temperature of 75 to 80° C., followed by emulsification of the melted substance C in the melted substance B. Then, xanthorrizol was added to the mixtures in a concentration of 3.0, 0.1, 0.01 and 0.001%, respectively. Finally, spice was added to the mixtures which were adjusted to the final volume with distilled water.

TABLE 23

Facial cream containing xanthorrizol

| Facial Cream | Cream I | Cream II | Cream III | Cream IV |
|---|---|---|---|---|
| A | | | | |
| Xanthorrizol | 3.0% | 0.1% | 0.01% | 0.001% |
| B | | | | |
| Glycerin | 2.0% | 2.0% | 2.0% | 2.0% |
| Propyleneglycol | 2.0% | 2.0% | 2.0% | 2.0% |
| Chlorolauryl Sulfate | 8.0% | 8.0% | 8.0% | 8.0% |
| Stearin | 5.4% | 5.4% | 5.4% | 5.4% |
| Mineral Oil | 4.5% | 4.5% | 4.5% | 4.5% |
| C | | | | |
| Spice | 0.02% | 0.02% | 0.02% | 0.02% |
| Cetyl Alchohol | q.s. | q.s. | q.s. | q.s. |
| Distilled Water | q.s. | q.s. | q.s. | q.s. |
| Preservative | q.s. | q.s. | q.s. | q.s. |

4 ml of each cream containing the crude extract was taken to test-tubes, and mixed with 1 ml of acne-causing pathogen cultures. The test-tubes were incubated with shaking, and antibacterial activity in test-tubes was measured after 24 hours by counting viable cell numbers. The results are shown in Table 24.

TABLE 24

Antibacterial activity of facial creams containing xanthorrizol

| Acne-causing Pathogen | Test Solution | Viable Cell Count (cell number/ml) 0 hr | 24 hr |
|---|---|---|---|
| Propionibacterium acnes | Cream I | $3.0 \times 10^5$ | <1 |
| | Cream II | $3.0 \times 10^5$ | <1 |
| | Cream III | $3.0 \times 10^5$ | <1 |
| | Crean IV | $3.0 \times 10^5$ | $1.5 \times 10^2$ |
| | Control | $3.0 \times 10^5$ | $3.3 \times 10^4$ |
| Staphylococcus aureus | Cream I | $4.5 \times 10^5$ | <1 |
| | Cream II | $4.5 \times 10^5$ | <1 |
| | Cream III | $4.5 \times 10^5$ | <1 |
| | Cream IV | $4.5 \times 10^5$ | $3.4 \times 10^4$ |
| | Control | $4.5 \times 10^5$ | $4.1 \times 10^3$ |
| Staphylococcus epidermis | Cream I | $6.8 \times 10^5$ | <1 |
| | Cream II | $6.8 \times 10^5$ | <1 |
| | Cream III | $6.8 \times 10^5$ | <1 |
| | Cream IV | $6.8 \times 10^5$ | $4.3 \times 10^2$ |
| | Control | $6.8 \times 10^5$ | $5.1 \times 10^3$ |

As clearly demonstrated in Table 24, facial creams exhibited much stronger antibacterial activity against acne-causing pathogens, compared to that of the control groups.

EXAMPLE 10

Skin Safety Test

To test safety of the crude extract and xanthorrizol having antibacterial activity to human skin, a patch test was performed by employing 0.3% crude extract, 0.06% crude extract, 0.06% xanthorrizol, and petrolatum as a control: after 6 healthy volunteers wore patches on their skin for 48 hours, skin conditions were observed for 48 to 96 hours in terms of adverse effects caused by the patches(see: Agner T., Clinical grading of experimental skin reactions. In "Handbook of non-invasive methods and the skin", Serup, J.(ed.), CRC press, 575–578, 1995), whose results are summarized in Table 25.

TABLE 25

Patch test for crude extract and xanthorrizol

| | | Response | |
|---|---|---|---|
| Substance | Concentration (%) | False Positive Response | Weak Positive Response |
| Crude extract | 0.3% | — | — |
| Crude extract | 0.06% | — | — |
| Xanthorrizol | 0.06% | — | — |
| Control (vaseline) | | — | — |

As shown in Table 25, it was clearly demonstrated that both of xanthorrizol and crude extract do not cause adverse effects such as erythema, scarring or edema on skin, assuring their safe use for various antibacterial products.

As clearly illustrated and demonstrated as above, the present invention provides a process for producing xanthorrizol from *Curcuma xhanthorriza* Roxb. and novel uses of the same. Xanthorrizol of the present invention has a strong antibacterial activity with a broad spectrum under a high temperature. Therefore, xanthorrizol can be applied as an active ingredient for various antibacterial products such as antibacterial agent, tooth paste, oral cleanser, chewing gum, soap and cosmetics.

Although the preferred embodiments of the present invention have been disclosed for illustrative purpose, those who are skilled in the art will appreciate that various modifications, additions and substitutions are possible, without departing from the scope and spirit of the invention as disclosed in the accompanying claims.

What is claimed is:

1. An antibacterial composition comprising an antibacterially effective amount of xanthorrizol.

2. The antibacterial composition of claim 1, wherein the composition is formulated in a pharmaceutical dosage form selected from the group consisting of tablet, capsule, soft gelatin capsule, solution, ointment, plaster, granule, lotion, aerosol, suppository, cataplasma, cream, troche, paste, pill and injection.

3. The antibacterial composition of claim 1, wherein the antibacterial composition is formulated in an oral product.

4. The antibacterial composition of claim 3, wherein the oral product comprises a toothpaste, an oral cleanser or a chewing gum.

5. The antibacterial composition of claim 4, wherein the toothpaste comprises 0.001 weight % to 1.0 weight % of the xanthorrizol based on the total weight of the toothpaste.

6. The antibacterial composition of claim 4, wherein the oral cleanser comprises 0.0001 weight % to 0.1 weight % of the xanthorrizol based on the total weight of the oral cleanser.

7. The antibacterial composition of claim 4, wherein the chewing gum comprises 0.0001 weight % to 0.1 weight % of the xanthorrizol based on the total weight of the chewing gum.

8. The antibacterial composition of claim 1, wherein the antibacterial composition is formulated in a product of soap or cosmetics.

9. The antibacterial composition of claim 8, wherein the soap comprises 0.001 weight % to 5.0 weight % of the xanthorrizol based on the total weight of the soap.

10. The antibacterial composition of claim 8, wherein the cosmetics comprises 0.001 weight % to 3.0 weight % of the xanthorrizol based on the total weight of the cosmetics.

11. The antibacterial composition of claim 1, wherein the xanthorrizol is extracted from *Curcuma Xanthorriza* Roxb.

12. The antibacterial composition of claim 1, wherein the xanthorrizol is included in an crude extract of *Curcuma Xanthorriza* Roxb.

13. The antibacterial composition of claim 12, wherein the crude extract is obtained by an extraction, the extraction being selected from the group consisting of an organic solvent extraction, a supercritical fluid extraction, a microwave extraction and an ultrasonic extraction.

14. The antibacterial composition of claim 13, wherein the organic solvent extraction is carried out by using an organic solvent, the organic solvent being selected from the group consisting of methanol, ethanol, hexane, ethylacetate, chloroform and mixtures thereof.

15. The antibacterial composition of claim 13, wherein the supercritical fluid extraction is carried out by using carbon dioxide as a supercritical fluid under a pressure of 100 to 400 bar, at a temperature of 35 to 70° C.

16. The antibacterial composition of claim 13, wherein the microwave extraction is carried under a microwave condition of 2,450 MHz for 1 to 10 minutes at a temperature of 50 to 120° C., using a solvent, the solvent being selected from the group consisting of water, ethanol, methanol and hexane.

17. The antibacterial composition of claim 13, wherein the ultrasonic extraction is carried under a microwave condition of 2,450 MHz. for 1 to 10 minutes at a temperature of 50 to 120° C., using a solvent, the solvent being selected from the group consisting of water, ethanol, methanol and hexane.

* * * * *